(12) United States Patent
Pan et al.

(10) Patent No.: US 9,773,306 B2
(45) Date of Patent: *Sep. 26, 2017

(54) METHOD FOR QUANTIFYING CARIES

(71) Applicant: Carestream Health, Inc., Rochester, NY (US)

(72) Inventors: Liangliang Pan, Shanghai (CN); Jiayong Yan, Shanghai (CN); Wei Wang, Shanghai (CN); Lixing Shi, Shanghai (CN); Victor C. Wong, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 48 days.

This patent is subject to a terminal disclaimer.

(21) Appl. No.: 14/197,637

(22) Filed: Mar. 5, 2014

(65) Prior Publication Data

US 2014/0185892 A1  Jul. 3, 2014

Related U.S. Application Data

(63) Continuation of application No. 12/487,729, filed on Jun. 19, 2009, now Pat. No. 8,768,016.

(51) Int. Cl.
*G06K 9/00* (2006.01)
*G06T 7/00* (2017.01)
*A61B 5/00* (2006.01)

(52) U.S. Cl.
CPC .......... *G06T 7/0012* (2013.01); *A61B 5/0088* (2013.01); *G06T 7/00* (2013.01);
(Continued)

(58) Field of Classification Search
None
See application file for complete search history.

(56) References Cited

U.S. PATENT DOCUMENTS 4,479,499 A  10/1984  Alfano
4,515,476 A   5/1985  Ingmar
(Continued)

FOREIGN PATENT DOCUMENTS

EP  2 083 389  7/2009
EP  2 312 527  4/2011
(Continued)

OTHER PUBLICATIONS

Ricardo Fabbri, Luciano Da F. Costa, Julio C. Torelli and Odemir M. Bruno "2D Euclidean distance transform algorithms: a comparative survey", ACM computing surveys 40, 2008, 44 pages.
(Continued)

*Primary Examiner* — Nancy Bitar

(57) ABSTRACT

A method for quantifying caries, executed at least in part on data processing hardware, the method comprising generating a digital image of a tooth, the image comprising intensity values for a region of pixels corresponding to the tooth, gum, and background; extracting a lesion area from sound tooth regions by identifying tooth regions, extracting suspicious lesion areas, and removing false positives; identifying an adjacent sound region that is adjacent to the extracted lesion area; reconstructing intensity values for tooth tissue within the lesion area according to values in the adjacent sound region; and quantifying the condition of the caries using the reconstructed intensity values and intensity values from the lesion area.

20 Claims, 10 Drawing Sheets

(52) U.S. Cl.
CPC ........... *G06T 2207/10024* (2013.01); *G06T 2207/10064* (2013.01); *G06T 2207/20212* (2013.01); *G06T 2207/30036* (2013.01)

(56) References Cited

U.S. PATENT DOCUMENTS

| | | | |
|---|---|---|---|
| 4,941,164 A | 7/1990 | Schuller et al. | |
| 6,231,338 B1* | 5/2001 | de Josselin de Jong | A61B 5/0088 433/215 |
| 7,179,066 B2 | 2/2007 | Good et al. | |
| 7,270,543 B2* | 9/2007 | Stookey | A61B 5/0088 433/215 |
| 7,305,111 B2 | 12/2007 | Arimura et al. | |
| 8,131,058 B2 | 3/2012 | Shimura | |
| 8,311,302 B2* | 11/2012 | Yan | A61B 5/0088 382/128 |
| 8,371,848 B2* | 2/2013 | Okawa | A61B 1/24 433/29 |
| 8,447,087 B2* | 5/2013 | Wong | A61B 1/00009 348/66 |
| 9,020,236 B2* | 4/2015 | Wang | A61B 5/0088 382/132 |
| 9,095,313 B2* | 8/2015 | Tolkowsky | A61B 5/064 |
| 9,305,334 B2* | 4/2016 | Barzelay | G06T 5/009 |
| 2004/0184643 A1 | 9/2004 | Stantchev et al. | |
| 2004/0202356 A1 | 10/2004 | Stookey et al. | |
| 2004/0240716 A1* | 12/2004 | de Josselin de Jong | A61B 5/0088 382/128 |
| 2005/0010106 A1* | 1/2005 | Lang | A61B 6/469 600/425 |
| 2005/0201618 A1 | 9/2005 | Tek | |
| 2005/0244794 A1 | 11/2005 | Kemp et al. | |
| 2005/0283058 A1 | 12/2005 | Choo-Smith et al. | |
| 2005/0283065 A1* | 12/2005 | Babayoff | A61B 1/00009 600/407 |
| 2006/0239526 A1* | 10/2006 | Jonusauskas | A61B 5/682 382/128 |
| 2006/0262988 A1 | 11/2006 | Tek et al. | |
| 2007/0019858 A1 | 1/2007 | Shimura | |
| 2007/0021670 A1 | 1/2007 | Mandelis et al. | |
| 2007/0053491 A1 | 3/2007 | Schildkraut et al. | |
| 2007/0081718 A1 | 4/2007 | Rubbert et al. | |
| 2007/0099148 A1 | 5/2007 | Wong et al. | |
| 2007/0248931 A1* | 10/2007 | Wong | A61B 5/0088 433/29 |
| 2008/0056551 A1 | 3/2008 | Wong et al. | |
| 2008/0062429 A1 | 3/2008 | Liang et al. | |
| 2008/0063998 A1 | 3/2008 | Liang et al. | |
| 2008/0170764 A1* | 7/2008 | Burns | A61B 5/0088 382/128 |
| 2009/0238457 A1 | 9/2009 | Rittscher et al. | |
| 2010/0322490 A1* | 12/2010 | Pan | A61B 5/0088 382/128 |
| 2011/0085713 A1* | 4/2011 | Yan | G06T 7/0081 382/128 |
| 2011/0085714 A1 | 4/2011 | Yan et al. | |
| 2011/0085715 A1* | 4/2011 | Yan | G06T 7/0081 382/128 |
| 2012/0148986 A1 | 6/2012 | Yan et al. | |
| 2013/0038710 A1* | 2/2013 | Inglese | A61B 5/0071 348/66 |
| 2014/0037180 A1* | 2/2014 | Wang | A61B 5/0088 382/132 |
| 2014/0185892 A1* | 7/2014 | Pan | A61B 5/0088 382/128 |
| 2016/0022389 A1* | 1/2016 | Esbech | G01J 3/513 250/208.1 |

FOREIGN PATENT DOCUMENTS

| | | |
|---|---|---|
| WO | 2004/104927 | 12/2004 |
| WO | 2008/027323 A2 | 3/2008 |
| WO | 2010/083623 | 7/2010 |

OTHER PUBLICATIONS

Duda, R. and Hart, P., *Pattern Classification and Scene Analysis*, John Wiley and Sons, 1973, pp. 271-272.
Hong Chen, Anil K. Jain, "Tooth contour extraction for matching dental radiographs", ICPR 2004, 4 pages.
Anil K. Jain, Hong Chen, "Matching of dental x-ray images for human identification", *Pattern Recognition* vol. 37, pp. 1519-1532, 2004.
European Search Report, Application No. EP 10 01 3639, dated May 30, 2011, 2 pages.
European Search Report, Application No. EP 10 013 637, dated May 31, 2011, 3 pages.
European Search Report dated May 30, 2011 for Application No. 10 013 638.1, 3 pages.
European Search Report dated Jan. 25, 2013, Application No. EP 10 006 356, 3 pages.
M. Mokhtari et al., "Feature detection on 3-D images of dental imprints," Proceedings of the IEEE Workshop on Biomedical Image Analysis, Jun. 1994, pp. 287-296.
L. Vincent, "Morphological Grayscale Reconstruction: Definition, Efficient Algorithm and Applications in Image Analysis," Proceedings of the Computer Society Conference on Computer Visions and Pattern Recognition, Jun. 1992, pp. 633-635.
Luc Vincent, "Morphological grayscale reconstruction in image analysis: applications and efficient algorithms", IEEE Transaction on Image Processing, vol. 2, No. 2, pp. 176-201, 1993.
Rosenfeld, A. and Pfaltz, J. "Sequential operations in digital picture processing", J. ACM. 13, 1966, 24 pages.
Commonly Assigned co-pending U.S. Appl. No. 12/578,806, entitled: "Method for Extracting a Carious Lesion Area", filed Oct. 14, 2009, by Jiayong Yan, et al.
Commonly Assigned co-pending , WO Application No. PCT/CN2009/000078, entitled "Method for Detection of Caries," Filed on Jan. 20, 2009, by Wei Wang, et al.
Rick et al., "Quantitative Modelling of Microcalcification Detection in Digital Mammography", MICCAI, LNCS 1679, 1999, pp. 32-42.
I.A. Pretty, "Quantification of dental plaque in the research environment", Journal of Dentistry, 2005, vol. 33, pp. 193-207.
I.A. Pretty, "Caries detection and diagnosis: Novel technologies", Journal of Dentistry, vol. 34, 2006, pp. 727-739.
Mukhopadhyay et al., "Multiscale Morphological Segmentation of Gray-Scale Images", IEEE Transactions on Image Processing, vol. 12, No. 5, May 2003, pp. 533-549.
European Search Report, Application No. EP 10013637, dated May 31, 2011, 3 pages.

* cited by examiner

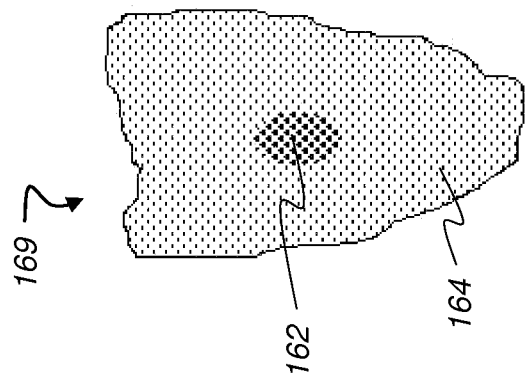
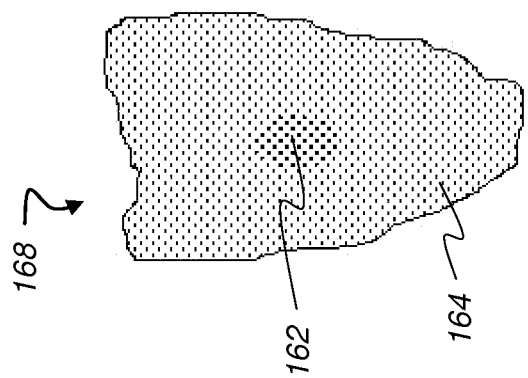
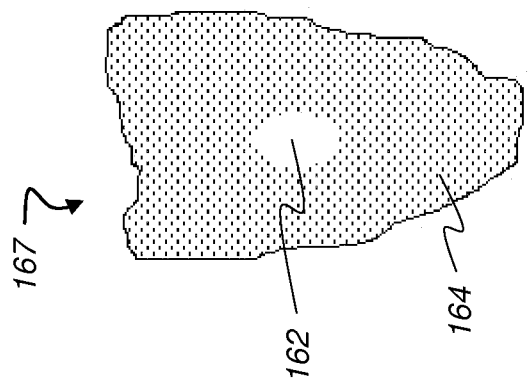

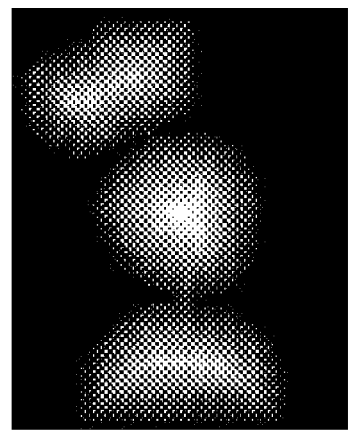
FIG. 5A
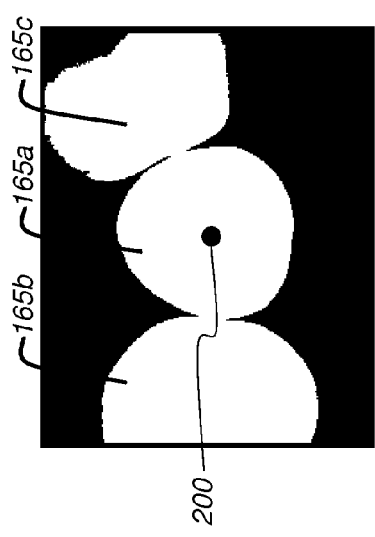
FIG. 5B
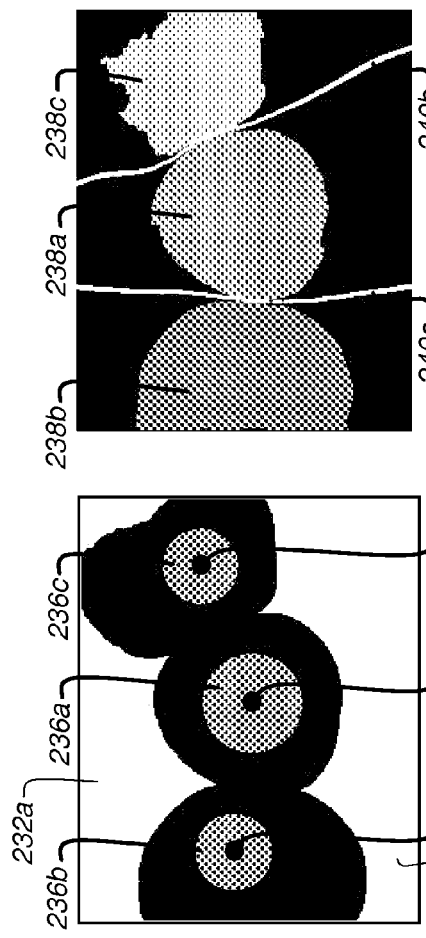
FIG. 5E
FIG. 5D
FIG. 5C
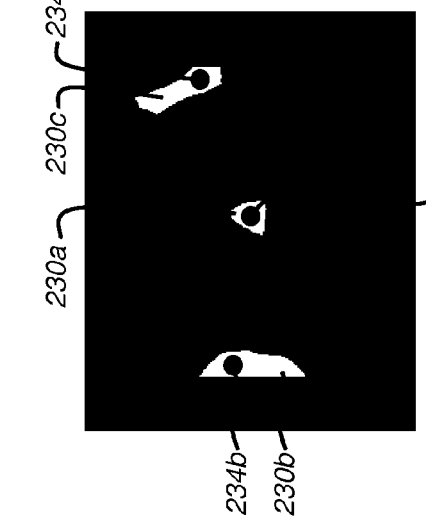

METHOD FOR QUANTIFYING CARIES

CROSS REFERENCE TO RELATED APPLICATIONS

This application is a Continuation of U.S. Ser. No. 12/487,729 filed on Jun. 19, 2009 entitled "METHOD FOR QUANTIFYING CARIES", in the name of Pan et al, which is incorporated herein in its entirety.

FIELD OF THE INVENTION

The invention relates generally to the field of dental imaging, and in particular to a method and an apparatus for early detection of caries. More specifically, the invention relates to a method and an apparatus for quantifying caries in tooth images captured using fluorescence and scattering of light.

BACKGROUND OF THE INVENTION

While there have been improvements in detection, treatment and prevention techniques, dental caries remains a prevalent condition affecting people of all age groups. If not properly and promptly treated, caries could lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time a caries condition is evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method employs fluorescence wherein teeth are illuminated with high intensity blue light. This technique, sometimes termed quantitative light-induced fluorescence (QLF), operates on the principle that sound, healthy tooth enamel yields a higher intensity of fluorescence under excitation from some wavelengths than does de-mineralized enamel that has been damaged by caries infection. The correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

Applicants note some references related to optical detection of caries.

U.S. Pat. No. 4,515,476 (Ingmar) describes the use of a laser for providing excitation energy that generates fluorescence at some other wavelength for locating carious areas.

U.S. Pat. No. 6,231,338 (de Josselin de Jong et al.) describes an imaging apparatus for identifying dental caries using fluorescence detection.

U.S. Patent Application Publication No. 2004/0240716 (de Josselin de Jong et al.) describes methods for improved image analysis for images obtained from fluorescing tissue.

U.S. Pat. No. 4,479,499 (Alfano) describes a method for using transillumination to detect caries based on the translucent properties of tooth structure.

Among products for dental imaging using fluorescence behavior is the QLF Clinical System from Inspektor Research Systems BV, Amsterdam, The Netherlands. The Diagnodent Laser Caries Detection Aid from KaVo Dental Corporation, Lake Zurich, Ill., USA, detects caries activity monitoring the intensity of fluorescence of bacterial by-products under illumination from red light.

U.S. Patent Application Publication No. 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescent image.

While the described methods and apparatus are intended for non-invasive, non-ionizing imaging methods for caries detection, there is still room for improvement. One recognized drawback with existing techniques that employ fluorescence imaging relates to image contrast. The image provided by fluorescence generation techniques such as QLF can be difficult to assess due to relatively poor contrast between healthy and infected areas. As noted in the '2356 Stookey et al. disclosure, spectral and intensity changes for incipient caries can be very slight, making it difficult to differentiate non-diseased tooth surface irregularities from incipient caries.

Overall, it is recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this shortcoming, the use of fluorescence effects appears to have some practical limits that prevent accurate diagnosis of incipient caries. As a result, a caries condition may continue undetected until it is more serious, requiring a filling, for example.

Detection of caries at very early stages is of particular interest for preventive dentistry. As noted earlier, conventional techniques generally fail to detect caries at a stage at which the condition can be reversed. As a general rule of thumb, incipient caries is a lesion that has not penetrated substantially into the tooth enamel. Where such a caries lesion is identified before it threatens the dentin portion of the tooth, remineralization can often be accomplished, reversing the early damage and preventing the need for a filling. More advanced caries, however, grows increasingly more difficult to treat, most often requiring some type of filling or other type of intervention.

To take advantage of opportunities for non-invasive dental techniques to forestall caries, it is necessary that caries be detected at the onset. In many cases, as is acknowledged in the '2356 Stookey et al. disclosure, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

In commonly-assigned U.S. Patent Application Publication No. 2008/0056551, a method and apparatus that employs both the reflectance and fluorescence images of the tooth is used to detect caries. It takes advantage of the observed back-scattering, or reflectance, for incipient caries and in combination with fluorescence effects, to provide an improved dental imaging technique to detect caries. The technique, referred to as Fluorescence Imaging with Reflectance Enhancement (FIRE), helps to increase the contrast of images over that of earlier approaches, and also makes it possible to detect incipient caries at stages when preventive measures are likely to take effect. Advantageously, FIRE detection can be accurate at an earlier stage of caries infection than has been exhibited using existing fluorescence approaches that measure fluorescence alone. The application describes a downshifting method to generate the FIRE image.

Commonly-assigned copending PCT/CN2009/000078, entitled METHOD FOR DETECTION OF CARIES describes a morphological method for generating a FIRE image with reduced sensitivity to illumination variation.

Quantification of caries based on a digital image of a tooth such as a fluorescence image provides numerical information on the severity of lesion regions and can help dentists make and carry out treatment plans. It can be a useful tool in the longitudinal monitoring of caries for dentists to observe the evolution of each lesion area over time. U.S. Patent Application Publication No. 2004/0240716 has disclosed some methods for quantification of caries; however, the disclosed methods generally require manual extraction of lesion regions from sound tooth areas of the image by the user, and they are based on fluorescence-only images. Manual extraction of lesion regions from the image presents two problems. Firstly, the extraction process is slow, requiring the user to make many mouse clicks or to draw lines on the images to indicate the boundary of a lesion region. Secondly, manual extraction requires considerable caries diagnostic experience on the part of the user and is generally subjective. In addition, fluorescence-only images display incipient caries at relatively low contrast, further adding difficulty to the manual lesion extraction process. Therefore, in the disclosed methods, only compromised caries quantification results are achieved at best.

Thus, it can be seen that there is a need for an improved method for quantifying caries in a tooth image, comprising a step of automatically extracting lesion regions from sound tooth regions based on a digital image of a tooth, particularly based on a FIRE image or fluorescence image of a tooth.

SUMMARY OF THE INVENTION

An object of the present invention is to provide a method for quantifying caries in a digital image of a tooth, especially in earlier stages of caries.

Another object of the present invention is to provide a method for quantifying caries based a FIRE image of a tooth.

A feature of the present invention is that carious lesions are automatically extracted in a FIRE image, the high contrast in the FIRE image providing improved sensitivity and accuracy for the identification of caries.

An advantage of the present invention is that carious lesions in tooth images are extracted and quantified without user intervention, thus providing an efficient workflow in caries identification and monitoring.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for quantifying caries, executed at least in part on data processing hardware such as computer hardware, the method comprising steps of generating a digital image of a tooth, the image comprising actual intensity values for a region of pixels corresponding to the tooth, gum, and background; extracting a lesion area from sound tooth regions by identifying tooth regions, extracting suspicious lesion areas, and removing false positives; identifying an adjacent sound region that is adjacent to the extracted lesion area; reconstructing intensity values for tooth tissue within the lesion area according to values in the adjacent sound region; and quantifying the condition of the caries using the reconstructed intensity values and intensity values from the lesion area.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 2A, 2B, 2C show illustratively a typical reflectance image, a fluorescence image, and a FIRE image, respectively.

FIG. 5A shows a binary image of three teeth similar to FIG. 4A.

FIG. 5B shows a distance image Idist formed from a distance transformation on the image of FIG. 5A.

FIG. 5C shows seed points in seeded areas.

FIG. 5D shows internal and external markers.

FIG. 5E is an illustration of interlines after the marker-controlled watershed and distance transform processing.

DETAILED DESCRIPTION OF THE INVENTION

Figure 1:
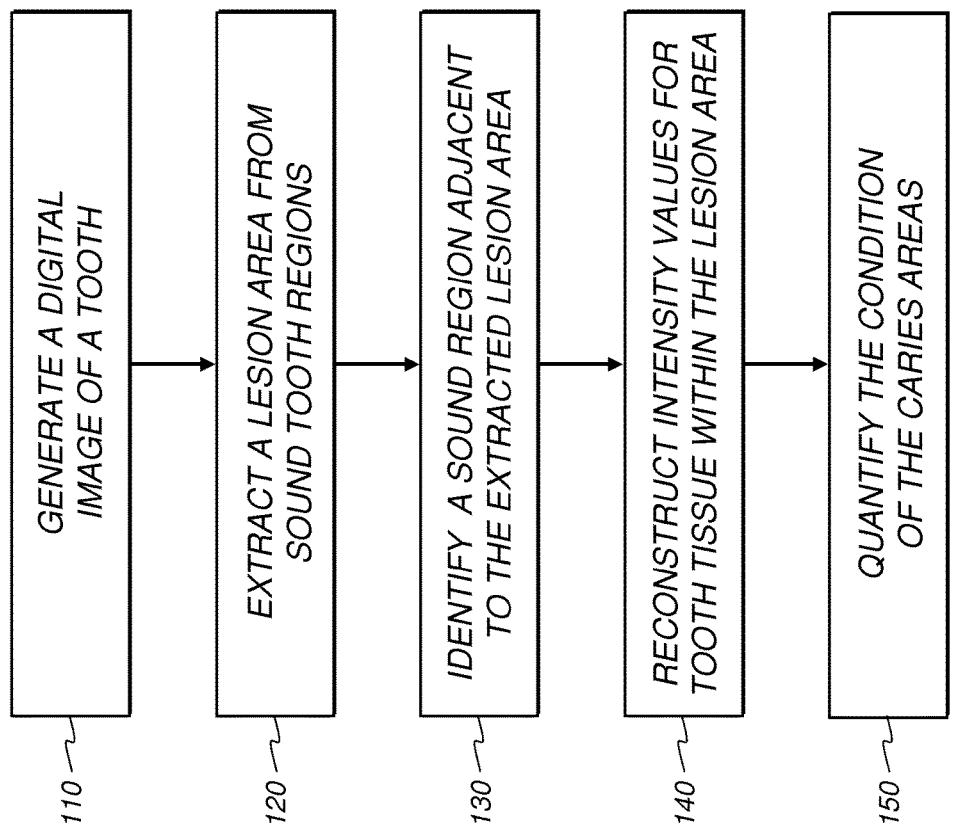
FIG. 1 shows a method for quantifying caries comprising five steps according to the present invention.

The following is a detailed description of the preferred embodiments of the invention, reference being made to the drawings in which the same reference numerals identify the same elements of structure in each of the several figures.

Reference is made to PCT/CN2009/000078, filed on Jan. 20, 2009, entitled METHOD FOR DETECTION OF CARIES, by Wei Wang et al.

Reference is made to U.S. Patent Application Publication No. 2008/0056551, published Mar. 6, 2008, entitled METHOD FOR DETECTION OF CARIES, by Wong et al.

Reference is made to U.S. Patent Application Publication No. 2008/0063998, published Mar. 13, 2008, entitled APPARATUS FOR CARIES DETECTION, by Liang et al.

Reference is made to U.S. Patent Application Publication No. 2008/0170764, published Jul. 17, 2008, entitled SYSTEM FOR EARLY DETECTION OF DENTAL CARIES, by Burns et al.

Reference is made to U.S. Patent Publication No. 2007/0099148, published on May 3, 2007, entitled METHOD AND APPARATUS FOR DETECTION OF CARIES, by Wong et al.

This invention includes calculation steps. Those skilled in the art will recognize that these calculation steps may be performed by data processing hardware that is provided with instructions for image data processing. Because such image manipulation systems are well known, the present description is directed more particularly to algorithms and systems that execute the method of the present invention. Other aspects of such algorithms and systems, and data processing hardware and/or software for producing and otherwise processing the image signals may be selected from such systems, algorithms, components and elements known in the art. Given the description as set forth in the following specification, software implementation lies within the ordinary skill of those versed in the programming arts.

The stored instructions of such a software program may be stored in a computer readable storage medium, which may comprise, for example: magnetic storage media such as a magnetic disk or magnetic tape; optical storage media such as an optical disc, optical tape, or machine readable bar code; solid state electronic storage devices such as random access memory (RAM), or read only memory (ROM); or any other physical device or medium employed to store a computer program. Using such software, the present invention can be utilized on a data processing hardware apparatus, such as a computer system or personal computer, or on an embedded system that employs a dedicated data processing component, such as a digital signal processing chip.

In this disclosure, the word "intensity" is used to refer to light level, and is also broadly used to refer to the value of a pixel in a digital image.

The term "water basin" as used herein is a term of art used to describe a structure that is identified and used in executing a marker-controlled watershed transformation in the imaging arts. The term "catchment basin" is sometimes used in the same way. References in this disclosure to "water basin" refer to this imaging arts construct.

Referring to FIG. 1, a method for quantifying caries, executed at least in part on data processing hardware such as computer hardware, comprises a step 110 of generating a digital image of a tooth, the image comprising actual intensity values for a region of pixels corresponding to the tooth, gum, and background; a step 120 of extracting a lesion area from sound tooth regions by identifying tooth regions, extracting suspicious lesion areas, and removing false positives; a step 130 of identifying a sound region that is adjacent to the extracted lesion area; a step 140 of reconstructing intensity values for tooth tissue within the lesion area according to values in the adjacent sound region; and a step 150 of quantifying the condition of the caries using the reconstructed intensity values and intensity values from the lesion area. Note that the phrase "extracting a lesion area," as used throughout this application, means identifying at least one lesion area in a digital tooth image.

FIGS. 2A, 2B, and 2C show illustratively a typical reflectance image 167, a fluorescence image 168, and a FIRE image 169, respectively, of a tooth surface including a sound tooth area 164 and an early lesion area (or caries region) 162. Generally, in a reflectance image, such as a white light reflectance image, the intensity of early caries regions is higher than that of their surrounding sound areas. In contrast, in a fluorescence image, such as one obtained under blue excitation light, the intensity of caries regions is lower than that of their surrounding sound areas because of the fluorescence loss in caries regions. A FIRE image is obtained through subtracting regional maxima and dome regions of the reflectance image from the fluorescence image. As a result, the FIRE image has a similar appearance as a fluorescence image because both have lower intensity values in a lesion area than in a surrounding sound area. However, the FIRE image has higher contrast than a fluorescence image, making it potentially more sensitive in detecting caries. It should be noted that other images that are generated by combining image data for the fluorescence and reflectance images can also be used for substituting the FIRE image.

Figure 2D:
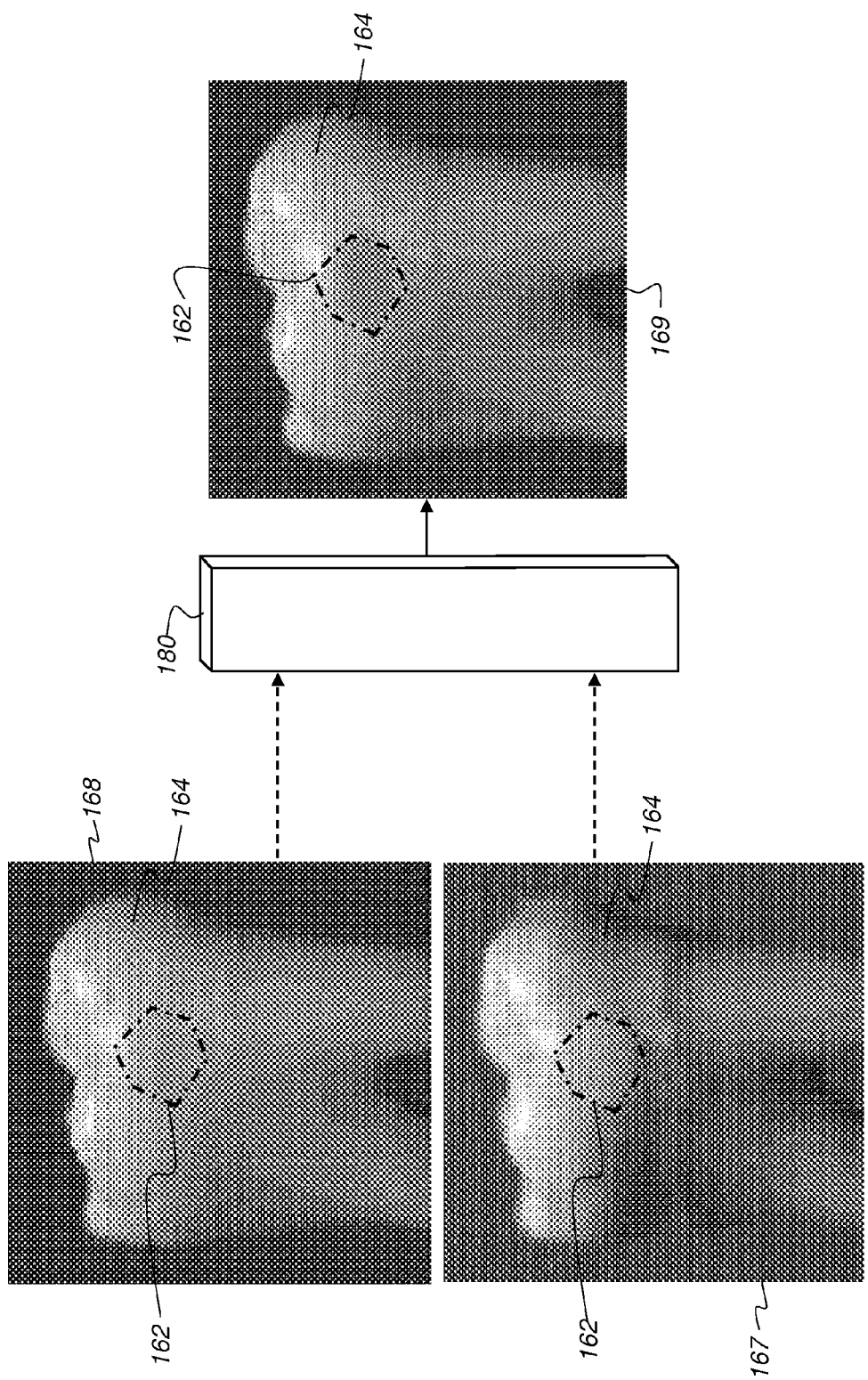
FIG. 2D is a view showing the process for combining dental image data to generate a FIRE image.

FIG. 2D corresponds to FIG. 5 of commonly-assigned copending U.S. Patent Application Publication No. 2008/0056551 (Wong et al.), entitled METHOD FOR DETECTION OF CARIES. This figure shows that a FIRE image 169 is formed by combining the fluorescence image 168 with the reflectance image 167 through a processing apparatus 180.

In the image processing field, there are many well known methods used to extract features from images, including but not limited to threshold, top-hat, and morphological grayscale reconstruction techniques (see Luc Vincent, "Morphological grayscale reconstruction in image analysis: applications and efficient algorithms", IEEE Transaction on Image Processing, Vol. 2, No. 2, pp. 176-201, 1993). However, not every technique is suitable for segmenting lesions from an image of a tooth. Teeth images have many characteristics that pose challenges for doing automatic lesion extraction. For example, a tooth image has no flat background (sound tooth areas are the background of the target caries), the caries have no fixed sizes and shapes, and surface contour and curvature of teeth cause uneven illumination, resulting in intensity variation across the tooth image. The present invention overcomes these difficulties by employing a combination of different image processing techniques that address the various problems specific to automatic processing of teeth images.

In the following, steps for quantifying caries according to the present invention are described referring to FIGS. 3A through 5E.

Step 110 of Generating a Digital Image of a Tooth

Figure 3B:
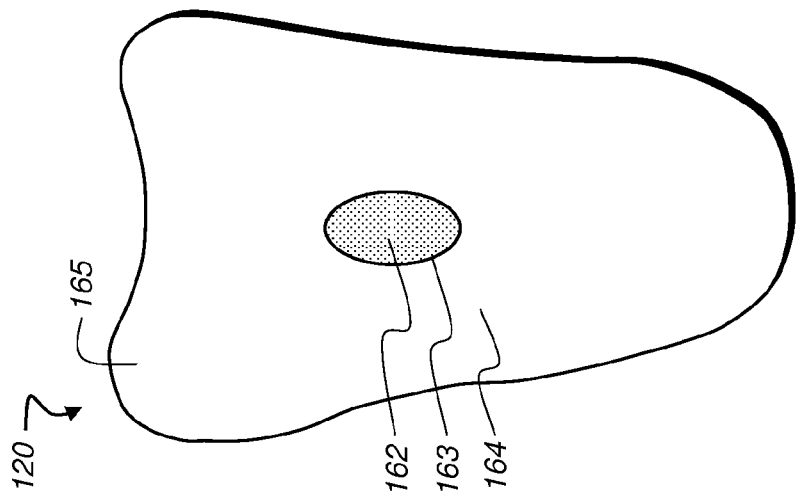
FIG. 3B shows a tooth region in a FIRE image having a lesion area identified in an extraction step.
Figure 3A:
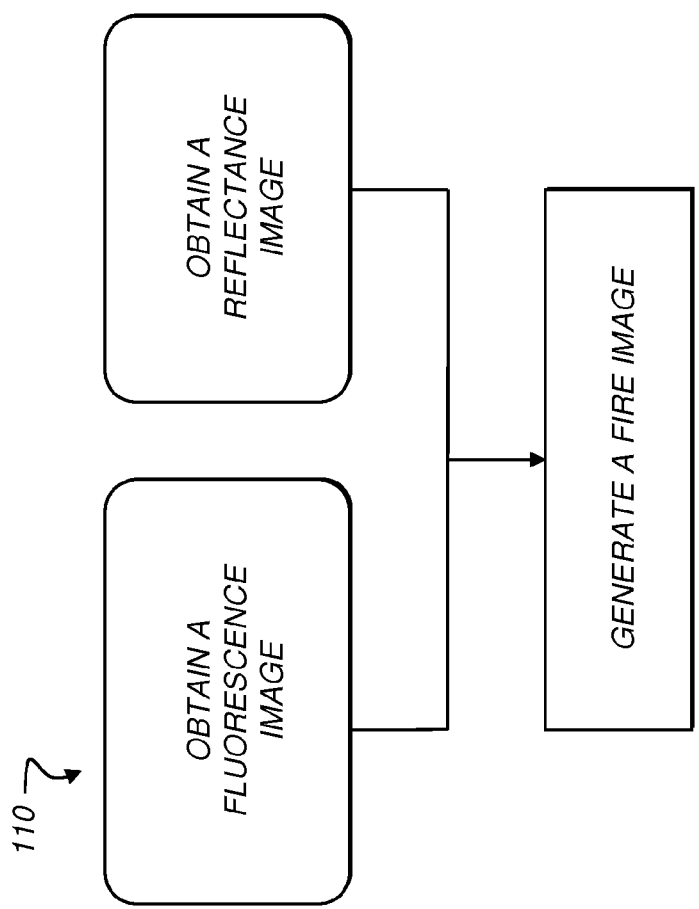
FIG. 3A shows an embodiment of a digital image generation step.

FIG. 3A shows one embodiment of step 110 of generating a digital image of a tooth, comprising steps of obtaining a fluorescence image, obtaining a reflectance image, and combining image data for the fluorescence and reflectance images to generate an image such as a FIRE image. Details of how the fluorescence and reflectance images are obtained are described in U.S. Patent Application Publication No. 2008/0063998, published Mar. 13, 2008, entitled APPARATUS FOR CARIES DETECTION, by Liang et al. According to this embodiment, the digital image of the tooth is a FIRE image 169, which is formed by combining the fluorescence image 168 with the reflectance image 167 through a processing apparatus 180 as shown in FIG. 2D.

The details of generating the FIRE image have been disclosed in the commonly-assigned copending PCT/CN2009/000078, entitled METHOD FOR DETECTION OF CARIES. Major steps of generating the FIRE image are as follows.

1. Obtaining a reflectance image, and then converting the reflectance image into a gray reflectance image with an intensity value of Iwgreen. The gray reflectance image can be the green channel of the reflectance image. This gray reflectance image is treated as a mask, and it has an intensity value of Imask=Iwgreen. In one example, the reflectance image is a white light reflectance image. The white light can be emitted from one or more white LEDs.

2. Generating a marker with an intensity value of Imarker according to the following formula, $$I_{marker} = I_{mask} - h_{dome},$$

where hdome, representing the height of a dome in the gray reflectance image, is a fixed value and is empirically selected based on the intensity values of a plurality of gray reflectance teeth images obtained. In one inventive example, hdome is 50.

3. Generating a reconstructed image having an intensity value of Ireconstructed through morphological grayscale reconstruction, which takes Imask and Imarker as input (see the Luc Vincent article, cited earlier).

4. Generating an image of regional *maxima* and dome regions of the gray reflectance image. This image, corresponding to the suspicious caries regions, has an intensity value $$I_{hdome} = I_{mask} - I_{reconstructed}.$$

5. Generating a FIRE image with an intensity value $$I_{FIRE} = I_{Fluo} - I_{hdome},$$

where $I_{FIRE}$ and $I_{Fluo}$ are the intensity values of the green channel of the generated FIRE image and the obtained fluorescence image, respectively. The generated FIRE image can be displayed as a color image by combining $I_{FIRE}$ with the red and blue channels of the fluorescence image. In one example, the fluorescence image is one obtained under blue excitation light. The blue light can be emitted from one or more blue LEDs. The FIRE image is the digital image used for subsequent image processing steps.

Another embodiment of step 110 of generating a digital image of a tooth comprises a step of obtaining a fluorescence image. The fluorescence image is the digital image used for subsequent image processing steps.

Step 120 of Extracting a Lesion Area from Sound Tooth Regions

Generally, a digital image of a tooth can be classified into three groups of regions: 1) gum, 2) tooth, and 3) other background. Caries detection only needs to be performed inside tooth regions 165.

Referring to FIG. 3B, inside the tooth region 165 is a lesion area 162, a surrounding sound tooth area 164, and segmentation border 163 that separates the two areas. Methods for identifying tooth region 165, lesion area 162, surrounding sound tooth area 164, and segmentation border 163 are described below.

Figure 3D:
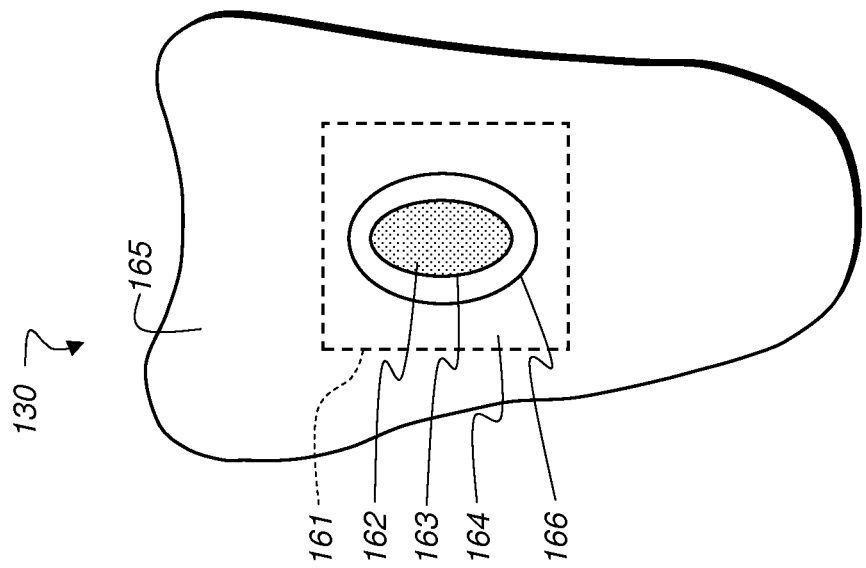
FIG. 3D shows a FIRE image with a dilated line in a sound tooth area, and a lesion segmentation border separating a sound tooth area and a lesion area after a sound region identification step.
Figure 3C:
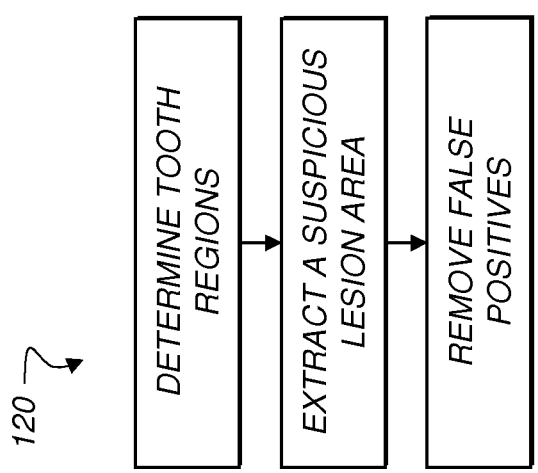
FIG. 3C shows an embodiment of a step for extracting a lesion area from sound tooth regions according to the present invention.

FIG. 3C shows an embodiment of step 120 for extracting a lesion area 162 from tooth regions 165 in a digital image of a tooth according to the present invention. Step 120 is performed automatically without a need for a user input. Specifically, step 120 includes sub-steps of identifying the tooth regions 165, extracting one or more suspicious lesion areas, and removing false positives. These sub-steps include details specific to tooth images, as discussed below.

Since some image processing work is done on a certain channel of a color image, for convenience, the following terms Iwred, Iwgreen, Iwblue, Ibred, Ibgreen, Ibblue, Ifred, Ifgreen, and Ifblue are used to represent the intensity values of the pixels in the red, green, and blue channels of the reflectance, fluorescence, and FIRE images, respectively. And in order to remove the impact of illumination level, intensity values of both reflectance and fluorescence images are adjusted to a range between 0 and 150, where 0 and 150 correspond to minimum and maximum intensity values.

As discussed, similar to the fluorescence image, the FIRE image has higher green intensity values inside normal/sound tooth areas than in caries and other background areas. Consequently, an adapted threshold technique is preferably used on a fluorescence or FIRE image to separate the tooth region, which contains both normal/sound tooth areas and caries areas, from the gum and other background.

Sub-Step of Identifying Tooth Regions 165

According to one embodiment of the present invention, tooth regions 165 are identified from the digital tooth image as follows. In this embodiment and other embodiments throughout the disclosure, grayscale versions of both the fluorescence and reflectance images are used, the grayscale images being generated from one channel of their respective color images, such as the green channel, or from a mixing of the three channels using methods well known in the image processing art. For illustrative purposes, the embodiment is described below using the green channels of the fluorescence and reflectance images, Ibgreen and Iwgreen, respectively.

Threshold images are generated from Ibgreen and Iwgreen by selecting intensity values higher than some predetermined threshold values $c1$ and $c2$, for example, 10 and 30, respectively. Secondly, the intersection regions of the two threshold images are taken as the preliminary tooth regions image Iroi0. Thirdly, a reference binary image Irefroi is obtained by thresholding the image Ifgreen with a threshold value $c3$ higher than the one used in generating Iroi0, such as 30. And lastly, a refined tooth regions 165 image, Iroi, is generated by choosing the regions that are in Iroi0 and connected to the objects in Irefroi. The above four steps increase the accuracy of selecting tooth regions 165 as compared to thresholding just the FIRE or fluorescence image. The refined tooth regions 165 image is then used in the following sub-steps of extracting suspicious lesion areas and removing false positives.

In an alternative embodiment, thresholding technique is applied to the fluorescence or FIRE image to determine tooth regions 165. This embodiment helps to provide simpler and faster processing.

Sub-Step of Extracting a Suspicious Lesion Area

In a FIRE image (Ifgreen), there is a definite morphological characteristic for caries, that is, the intensity of region of caries 162 is lower than that of the surrounding sound tooth area 164. The present invention takes advantage of this characteristic to detect and segment the suspicious caries areas based on mathematical morphology theory.

In one embodiment, a marker-controlled watershed based method is adapted to detect and segment the suspicious caries areas. The key to this method is to determine internal and external markers for the target objects. According to the present invention, the internal markers are determined with the morphological grayscale reconstruction technique. The same technique has also been used for generating a FIRE image as discussed above.

To determine internal markers with the morphological gray-scale reconstruction method, the regional basins Ihbasin are first detected; they correspond to the target regions of caries because they have lower intensity than surrounding sound areas. Then, the internal markers are obtained by thresholding Ihbasin with a fixed value, for example, 50. Note that the fixed value can be adjusted according to detection sensitivity requirement. The internal markers are the regions inside which the intensities of Ihbasin are higher than the given threshold value.

To obtain the external markers, a binary image is first formed from the internal markers, wherein the pixel value of the binary image is 1 for a pixel inside internal markers and is 0 otherwise. Then a distance transformation (DT), mapping each image pixel onto its shortest distance to the target objects, is applied to the binary image to generate a DT image (see "Sequential operations in digital picture processing", J. ACM. 13, 1966, by Rosenfeld, A. and Pfaltz, J. and "2D Euclidean distance transform algorithms: a comparative survey", ACM computing surveys 40, 2008, by Ricardo Fabbri, Luciano Da F. Costa, Julio C. Torelli and Odemir M. Bruno). The ridge lines that are composed of the pixels with local maximal values in the DT image and located between the internal markers are taken as the external markers.

Next, the gradient image of Ifgreen is calculated with the Sobel operator. The Sobel operator is an image processing function well known to those skilled in the image processing/pattern recognition art; a description of it can be found in *Pattern Classification and Scene Analysis*, Duda, R. and Hart, P., John Wiley and Sons, 1973, pp. 271-272.

With the internal and external markers and the gradient image identified or determined, marker-controlled watershed transformation is then applied to generate a contour of the target regions of caries 162 directly. A description of the marker-controlled watershed transformation can be found in "Morphological grayscale reconstruction in image analysis: applications and efficient algorithms", IEEE Transaction on Image Processing, Vol. 2, pp. 176-201, 1993, by Luc Vincent.

In another embodiment, a method based on morphological bottom-hat operation along with the multi-resolution and surface reconstruction techniques is adapted to detect and segment the suspicious caries areas. According to this embodiment of the present invention, a bottom-hat operation is first applied to Ifgreen to produce an original bottom-hat image with an intensity value of Ibothat. Then a multi-resolution strategy is adapted to enable detection of caries with different sizes. According to this strategy, the original bottom-hat image is down-sampled to form one or more reduced-resolution bottom-hat images, such as 2×-down sampled image and 4×-down sampled image. Given a 2-Dimensional shaped structure element with a fixed size, for example, a disk with a radius of 10 pixels, the morphological bottom hat is then applied to the images with different resolutions (that is, original bottom-hat image, 2×-down sampled bottom-hat image, 4×-down sampled bottom-hat image, etc.). Note that the 2-Dimensional structure element can take other shapes. The size of the structure element, for example, the radius of the disk, can be adjusted according to the image resolution or the size of the target objects. For each of the obtained multi-resolution bottom-hat images, according to the statistic of the intensity value inside the corresponding tooth regions, a threshold value Ithres is calculated as $$I\text{thres}=I\text{mean}+w*I\text{std},$$

where w is the weighting parameter determined experimentally, and Imean and Istd are the mean and standard deviation of intensity values, respectively. Applying a threshold operation to each of the multi-resolution bottom-hat images, a binary image is obtained, inside which the regions with a nonzero value are the initial suspicious caries areas in the image with corresponding resolution. After interpolating each of the binary images back to the original resolution to produce interpolated images, the union of all the interpolated images is taken as the initial suspicious lesion areas.

Since unable to use an infinite number of resolutions, and the size and shape of the structure elements are not the same as those of the target regions of caries 162, the initial suspicious caries areas are usually not the optimal results.

However, by using a small value of the weighting parameter w, the target caries areas can be included inside the initial suspicious caries areas with high confidence. In one example, the weighting parameter w is 1.0, 0.5, and 0 for the original, 2×-down sampled, and 4×-down sampled images, respectively. Certainly, the weighting parameter w can be adjusted according to practical requirements.

The normal intensity values (i.e., intensity values of the areas before the development of caries) inside the initial suspicious caries areas can be further estimated according to those outside the initial suspicious caries areas. According to the present invention, the intensity estimation is a surface reconstruction processing, generating Ireconstructed, where intensity is taken as a topological surface. Subtracting the original image Ifgreen from the reconstructed image Ireconstructed, a difference image Idiff is obtained. Because the intensity values inside the caries areas are lower than those of the normal/sound tooth areas, and the change between parts inside the normal or sound tooth areas is not as much as that between the caries and the normal/sound tooth areas, the regions with larger change in intensity values (for example, >7, which can be adjusted according to the required detection sensitivity) are taken as the refined suspicious caries areas.

While the morphological grayscale reconstruction technique could also be used to detect regional maxima-dome of a certain height or regional minima-basin of a certain depth in a grayscale image, it is not as suitable as the embodiments discussed above to extract caries lesion in teeth image. This is because different caries areas have different contrast with respect to their surrounding areas. Thus, different regional extrema heights or depths are needed to suit different images or different caries infections. After all, the height or depth is still a global parameter. Additionally, the morphological grayscale reconstruction is more difficult to be implemented and is slower than the morphological bottom-hat method of the present invention.

While a conventional top/bottom hat method might also be considered for use to detect regional maxima dome or minima basin regions, the method also is unsuitable in extracting caries lesion because it is difficult to determine the size of the structure element. This is unlike the morphological bottom-hat method of the present invention, which when used along with the multi-resolution and surface reconstruction techniques, successfully overcomes the problem of determining the size of the structure element.

Sub-Step of Removing False Positives

Based on experimental results, most occurrences of false positives can be grouped into two categories: (1) areas having low contrast (typically lower than 7, though it can be adjusted according to the practical application) compared to the surrounding areas, and (2) areas between the proximal surfaces of adjoining teeth (hereafter referred to as interproximal regions).

According to the present invention, the low contrast false positives are removed by calculating the intensity contrast between suspicious area and its surrounding area.

The interproximal false positives are removed according to the morphological features of the suspicious caries located inside or connected to the interproximal regions. To do this, the interproximal region is first identified.

A detailed description of how interproximal regions are located in teeth images is given below.

For adjoining teeth that are well separated, the interproximal regions contain spaces that are part of the background. This first kind of interproximal region having clear demarcation of the adjoining teeth is located as follows. Firstly, a distance transformation is applied to the binary image of tooth regions, and the pixel with the largest distance measured from the boundaries of the identified tooth regions in the binary image is located. Secondly, the identified tooth region that is connected to the located pixel is assigned as one object, and the other identified tooth regions are assigned as another object. And thirdly, the pixels in the background having the same distance to the two objects are then defined to be the interproximal regions.

For adjoining teeth that are very close to each other, the interproximal regions do not contain a clear demarcation of the adjoining teeth. Different image processing approaches have to be taken to identify this second kind of interproximal region in tooth images. In the first inventive example, referring to FIGS. 4A through 4E, the second kind of interproximal regions are located in four steps with marker-controlled watershed transformation and distance transformation in the region connected to the pixel with the largest distance.

Figure 4A:
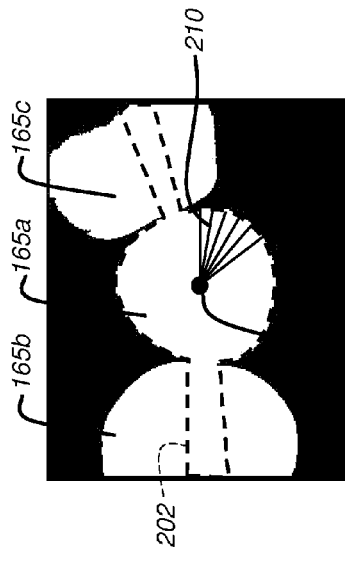
FIG. 4A shows a binary image of three teeth.

FIG. 4A shows a binary image of a target tooth 165a and two neighboring teeth 165b and 165c. The light areas represent the teeth, while the dark areas represent background of the teeth. The light and dark areas are separated by a boundary. The origin point 200 is defined as the pixel with the maximal distance to the boundaries of the teeth, though any point near the center of the target tooth 165a can also be chosen as the origin point. The origin point can also be determined with other methods according to practical applications. For example, if the tooth located at the center of the image is chosen as the target tooth, the local maxima point closest to the image center can be selected as the origin point.

Figure 4B:
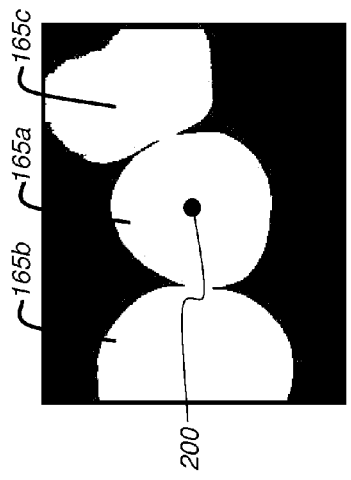
FIG. 4B shows a contour line formed from a fan of ray lines from the origin point.

In the first step as shown in FIG. 4B, a fan of ray lines 210 are cast from the origin point 200 in every direction between 0° and 360°. Subsequently a contour line 202 is formed or defined from points at which each ray line 210 first encounters the boundary between the light and dark areas.

Figure 4E:
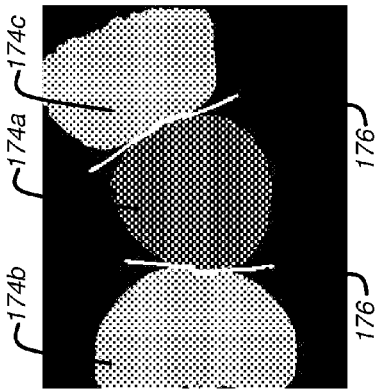
FIG. 4E is an illustration of interlines between adjoining teeth.
Figure 4D:
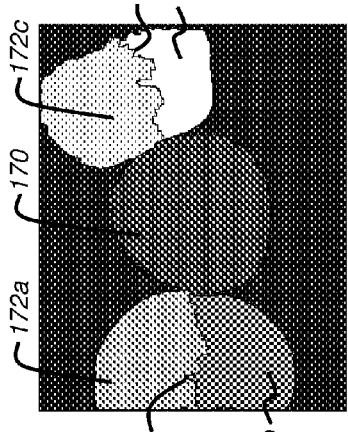
FIG. 4D is an illustration of the marker-controlled watershed result.
Figure 4C:
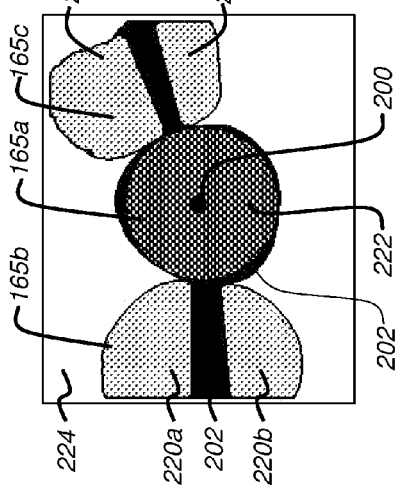
FIG. 4C shows determined internal and external markers.

In the second step, internal and external markers are identified or determined as follows. As shown in FIG. 4C, internal makers are determined from a certain circular area 222 around the origin point 200 and the gray areas 220a, 220b, 220c, 220d. According to one example of the present invention, the radius of the circular area 222 is chosen as ¾ times of the maximal distance, the distance of the origin point 200 to the tooth boundaries. The gray areas 220a, 220b, 220c, 220d are obtained by subtracting the area enclosed by the contour line 202 from the tooth areas 165a, 165b, 165c, which have been determined by the boundary between the light and dark areas in reference to FIG. 4A. The outer light areas 224, corresponding to the dark areas of FIG. 4A, are taken as the external markers.

In the third step, a marker-controlled watershed transformation is applied to a gradient image of a grayscale FIRE image with the above determined internal and external markers. In one embodiment, the grayscale FIRE image is generated from the green channel of the FIRE image, Ifgreen. In alternative embodiments, the grayscale FIRE image can be generated from a mixing of the three channels using methods well known in the image processing art. This transformation results in a water basin 170 connected to the internal marker that corresponds to the circular area 222 of FIG. 4C, and water basins 172a, 172b, 172c, 172d connected to the internal markers that correspond to the gray areas 220a, 220b, 220c and 220d of FIG. 4C, respectively. This transformation also results in watershed lines 173a, 173b. Watershed line 173a separates water basins 172a from 172b, while watershed line 173b separates water basins 172c from 172d. As noted earlier, the term "water basin", also referred to as catchment basin, is a term of the marker-controlled watershed transformation art in imaging, known to a person skilled in the art.

In the fourth step, the pixels having the same distance to the two groups of basins are then taken to be the second kind of interproximal regions. FIG. 4E shows parts of the interlines 176, indicating locations of the interproximal regions that are identified. Interlines 176 are obtained by marker-controlled watershed transformation and distance transformation. Region 174a is obtained from water basin 170. Region 174b is obtained from a combination of water basins 172a and 172b. A region 174c is obtained from a combination of water basins 172c and 172d.

In the second inventive example, referring now to FIGS. 5A through 5E, the second kind of interproximal regions that have no clear demarcation are located in four steps with a different adaptation of marker-controlled watershed transformation and distance transformation in the region connected to the pixel with the largest distance. Although sharing similar third and fourth steps, this second inventive example differs from the first inventive example in the first two steps.

Similar to FIG. 4A, FIG. 5A shows a binary image of a target tooth 165a and two neighboring teeth 165b and 165c. The light areas represent the teeth, while the dark areas represent background of the teeth.

In the first step as shown in FIG. 5B, a distance transformation is applied to the image of FIG. 5A and results in a distance image Idist, in which the pixel value represents the closest distance of that pixel to the background of the teeth.

In the second step shown in FIG. 5C and FIG. 5D, the internal markers 230a, 230b, 230c and external marker 232 are determined as follows.

With Idist as the mask and Idist−dhome as the marker, using morphological grayscale reconstruction, a reconstructed image Idrecon can be obtained. Then Iseeds can be determined according to the following equation:

$$Iseeds=(Idrecon>Tdrecon) \cap (Idist>Tdist),$$

where Tdrecon and Tdist are two threshold values (for example, Tdrecon=5, and Tdist=10), respectively. The symbol (Idrecon>Tdrecon) refers to the area in which the pixel values of Idrecon are greater than Tdrecon, and the symbol (Idist>Tdist) refers to the area in which the pixel values of Idist are greater than Tdrecon. The symbol ∩ is the intersection operator, familiar to those skilled in set theory.

Seeded regions 230a, 230b, 230c obtained from Iseeds are shown in FIG. 5C. In each seeded region, according to the distance image Idist in FIG. 5B, a seed point is identified as the pixel with maximal distance. For example, seed points 234a, 234b, and 234c are the pixels having maximal distance in seeded areas 230a, 230b, and 230c, respectively. Taking the seed point as the origin point and ¾ times of its distance as the radius, for each seeded region, a circular region is created as an internal marker corresponding to the seed point. Specifically, circular internal markers 236a, 236b, and 236c are created from seed points 234a, 234b, and 234c, respectively, as shown in FIG. 5D. The background regions of the teeth are used as the external markers 232a, 232b.

Similar to the third step of the first inventive example (in reference to FIGS. 4A through 4E), in the third step, as shown in FIG. 5E, marker-controlled watershed transformation is applied to the gradient image of a grayscale FIRE image with the above determined internal markers 236a, 236b, and 236c and external markers 232a, 232b, and water basin regions 238a, 238b, 238c for internal markers 236a, 236b, and 236c are obtained, respectively. Finally, in the fourth step, again similar to the fourth step of the first inventive example, interlines 240a, 240b are located as the pixels having the same distance to two neighboring water basin regions.

After the interproximal regions are located, the suspicious caries areas connected to the interproximal regions are then identified. Because some true caries are also located in these regions, not all the suspicious caries areas connected to the interproximal regions should be removed. A true caries often appears as a "grayscale hole", which is an area of dark pixels surrounded by lighter pixels in the grayscale image. Thus, the "grayscale hole" characteristic is used to test which of the suspicious caries areas are true caries and should be retained, while the other suspicious areas connected to the interproximal regions are removed as false positives.

After the false positives are removed, the remaining suspicious caries areas are the extracted regions of caries 162. These areas may be outlined or highlighted with false colors in a displayed FIRE, fluorescence, or reflectance image of the teeth to aid caries screening or diagnosis. They are also used for caries quantification analysis, in the steps described below.

Step 130 of Finding a Sound Tooth Region Adjacent to the Extracted Lesion Area

Referring back to FIG. 3D, step 130 of identifying a sound tooth region adjacent to the extracted lesion area is performed by expanding the suspicious lesion areas 162 outward to dilated line 166 with morphological dilation, an operation well known in the image processing art. This step is performed automatically without a need for user input. This step and steps 140 and 150 are preferably performed on the fluorescence image, for reasons explained below. The areas surrounding the expanded suspicious lesion areas are taken as the normal/sound areas, and the values of the pixels making up the dilated line 166 are taken as the intensity values of the surrounding normal/sound areas. The algorithmic implementation of the morphological dilation step is similar to that presented in FIG. 3 of commonly assigned co-pending U.S. Patent Application Publication No. 2008/0170764. This step reduces errors even if there are possible detection errors in the detected suspicious caries regions and in the non-significant intensity changes in normal/sound tooth areas.

Step 140 of Reconstructing Intensity Values for Tooth Tissue within the Lesion Area For assessing the severity of the extracted lesions and for monitoring the development of the identified lesions over time, it is helpful to have an estimate of the normal intensity values of the suspicious caries regions before the development of caries. This can be performed through various approaches based on the intensity values of the surrounding normal/sound areas found in Step 130.

In one embodiment, after the surrounding sound area is identified, the reconstructed intensity value for tooth tissue within the lesion area can be obtained using a bilinear interpolation technique according to values in the adjacent sound region as described below.

Figure 3E:
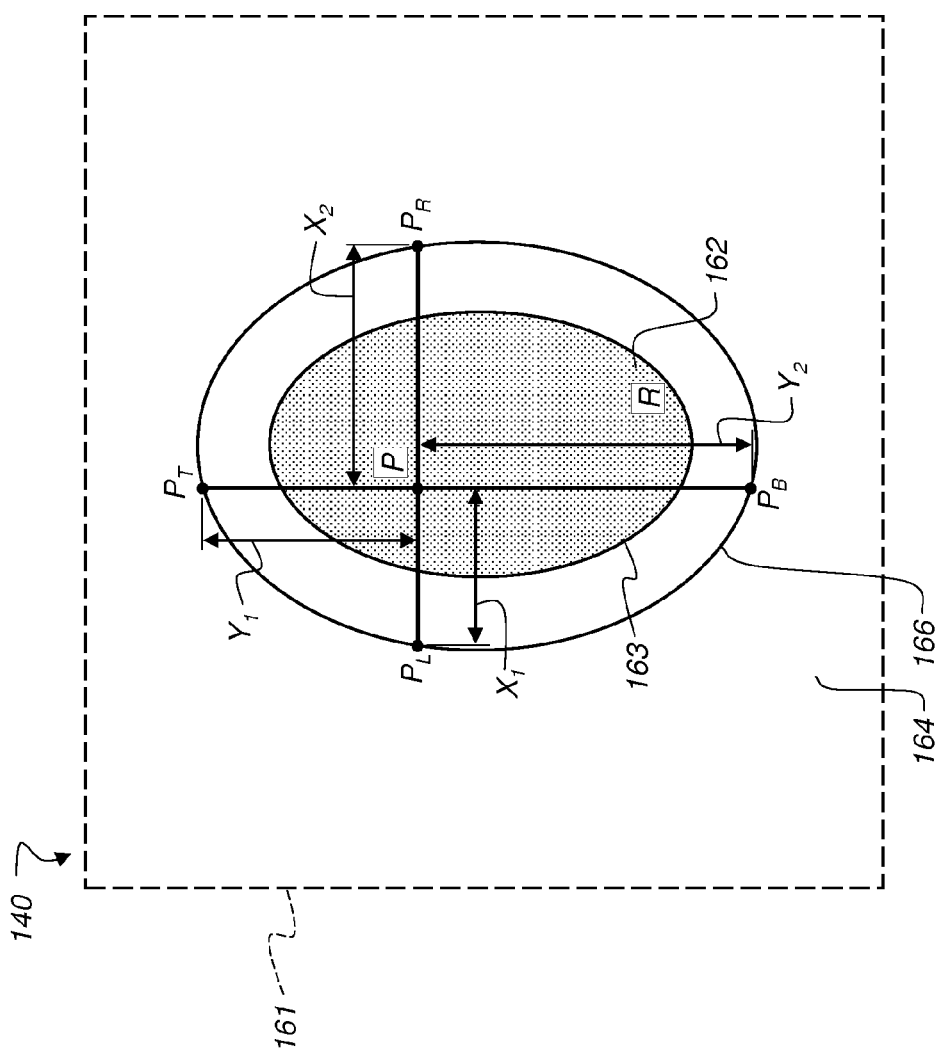
FIG. 3E shows an embodiment of an intensity reconstruction step using a bilinear interpolation.

FIG. 3E shows an exploded view of a region of interest 161 shown in FIG. 3D. For each pixel P in the lesion area R 162, there are four pixels on the dilated line 166 in the sound area that are to the left, right, top, and bottom of P, named $P_L$, $P_R$, $P_T$, $P_B$, respectively. The estimation of the reconstructed intensity value $I_r$ at P can be calculated using a bilinear interpolation, for which the formulae are shown below.

$$I_H = \frac{I_L \cdot x_2 + I_R \cdot x_1}{x_2 + x_1}$$

$$I_V = \frac{I_T \cdot y_2 + I_B \cdot y_1}{y_2 + y_1}$$

$$I_r = \frac{I_H + I_V}{2}$$

Bilinear interpolation is carried out in this way for every pixel in the region of caries 162 to reconstruct the normal intensity values for the whole region.

As an alternative embodiment, after the surrounding sound area is identified, the reconstructed intensity value for tooth tissue within the lesion area can be obtained using a surface fitting technique such as a two-dimensional spline, or Bézier fit.

Another alternative embodiment for reconstructing intensity value for tooth tissue within the lesion area is to smoothly interpolate inward from the pixel's values on the boundaries of the expanded suspicious caries areas by solving Laplace's equation. This embodiment is an adaptation of a common image processing technique (such as what has been implemented in the familiar Matlab software function "roifill" in its image processing toolbox), and results in more accurate estimation.

Step 150 of Quantifying the Condition of the Caries

As discussed above, quantitative information on the regions of caries 162 is helpful for assessing the condition of the extracted lesions and for monitoring the development of the identified lesions over time. The condition of caries in a tooth image can be quantified in a number of ways, including calculating the size (or area) of the lesion area and calculating fluorescence loss ratio of the lesion area.

In one example, the lesion area is calculated by counting the actual pixel number within the regions of caries 162, and then converting that to actual spatial dimension, such as mm².

In another example, the fluorescence loss is used to measure the condition of the caries. Fluorescence loss in tooth structure has been demonstrated to be a direct indication of the degree of demineralization in the structure. This quantity can be directly calculated from the intensity values in the tooth's fluorescence image. In the fluorescence image, the fluorescence loss ratio $\Delta F$ at each pixel within the lesion area is calculated using the formula below:

$$\Delta F = \frac{I_r - I_o}{I_r},$$

where $I_r$ is the reconstructed intensity value from step 140, and $I_o$ is the actual measured intensity value of the green channel of the fluorescence image $I_{Fluo}$. Where caries has occurred, $\Delta F > 0$.

The whole fluorescence loss L of the lesion region is the sum of $\Delta F$ within the lesion region R:

$$L = \sum_{i \in R} \Delta F_i$$

Figure 6A:
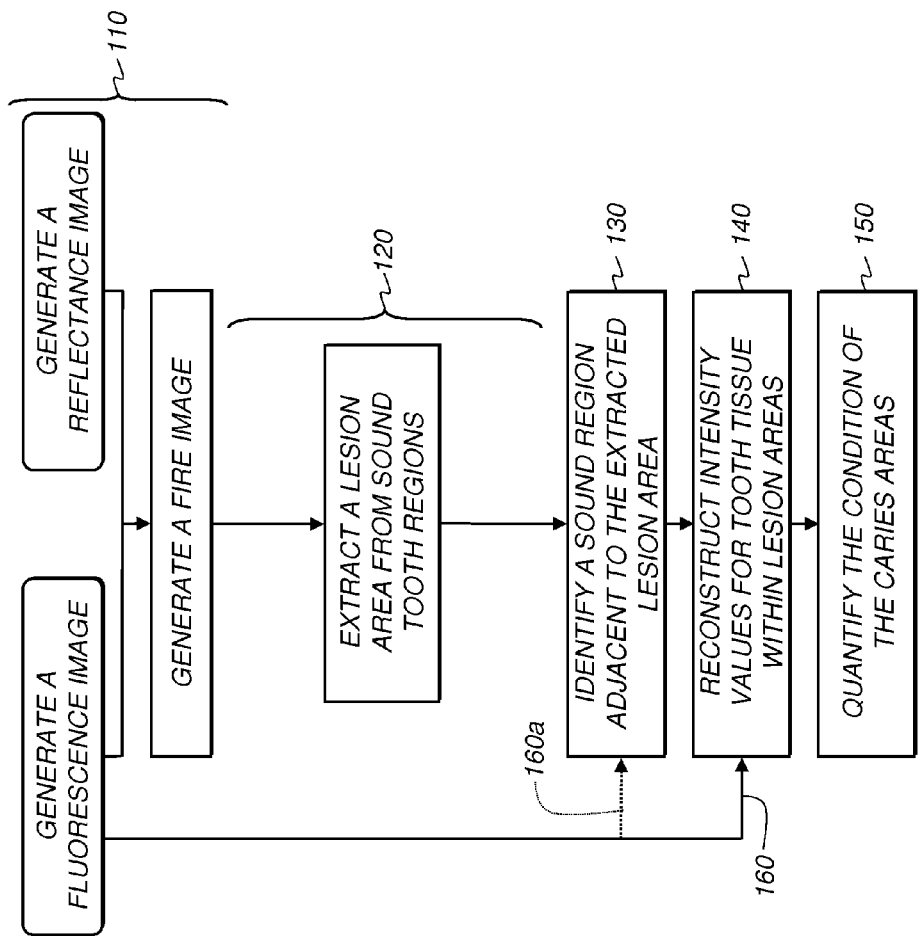
FIG. 6A shows a method for quantification of caries comprising a step of generating a FIRE image according to the present invention.

According to another embodiment of the present invention, FIG. 6A shows a method for quantification of caries comprising a step of generating a FIRE image or other images obtained by combining a fluorescence image and a reflectance image of the tooth according to the present invention. FIG. 6A is similar to FIG. 1. However, in FIG. 6A the digital image of the tooth is a FIRE image or the like which is generated from both a reflectance image and a fluorescence image. Particularly, the reflectance image is generated using white or single color light, while the fluorescence image is generated under excitation light in the ultraviolet-blue range. During step 130 of identifying a sound region adjacent to the extracted lesion area, the fluorescence image may substitute the FIRE image as input, indicated by the dashed arrow 160a. During step 140 of reconstructing intensity values within a lesion area and step 150 of quantifying the condition of the caries areas, the fluorescence image is also needed as input, indicated by the arrow 160.

Figure 6B:
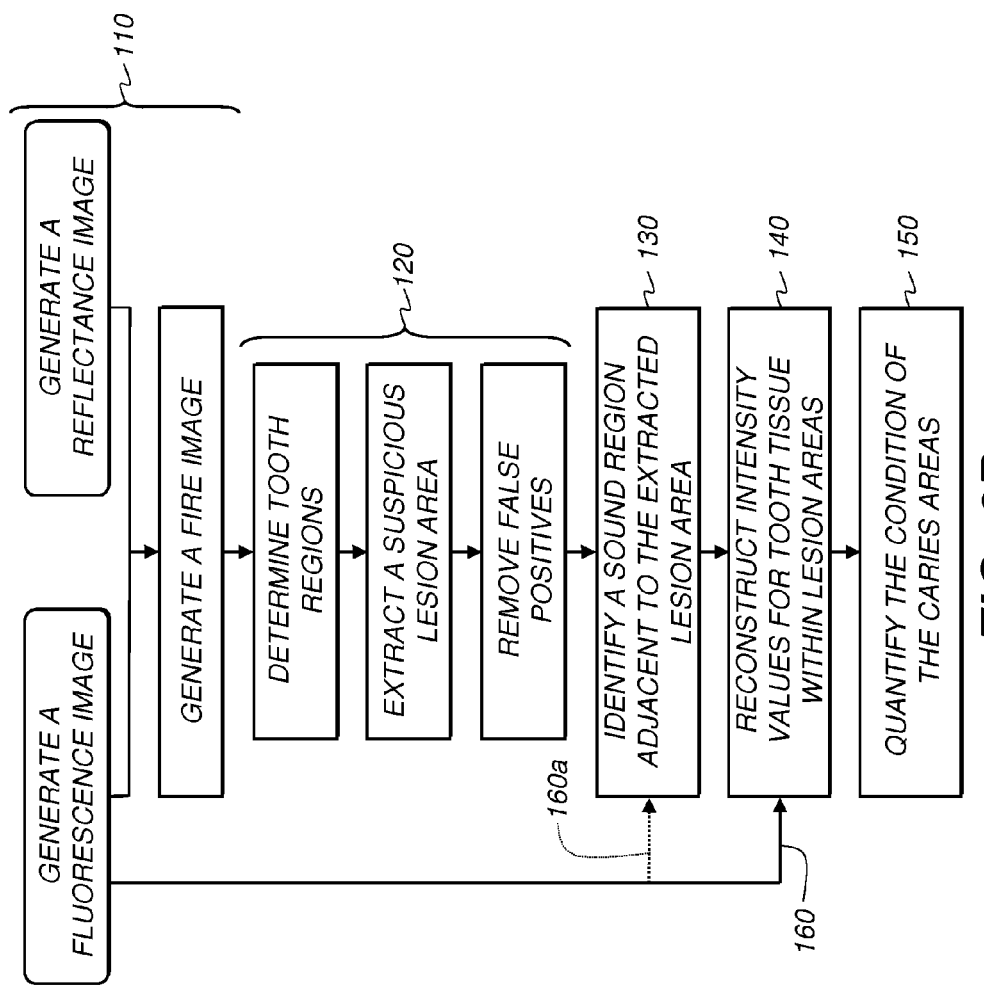
FIG. 6B shows a method for quantifying caries comprising a step of generating a FIRE image and sub-steps in step of extracting a lesion area from sound tooth regions according to the present invention.

FIG. 6B shows another embodiment of the prevent invention. It is similar to FIG. 6A, but differs in step 120 which specifically comprises steps of identifying the tooth regions 165 from a tooth image, extracting a suspicious lesion area, and removing false positives. The dashed arrow 160a shows that the fluorescence image may be used for step 130, and the arrow 160 shows that the fluorescence image is used for steps 140 and 150.

In another alternative embodiment, referring back to FIG. 1, the digital image generated in step 110 is a fluorescence image of the tooth. As discussed previously, the fluorescence image has similar characteristics as the FIRE image, and so the methods used in the lesion areas extraction step 120 can all be carried out on the fluorescence image. Therefore, in this alternative embodiment, the fluorescence image is used in all steps from Step 110 to Step 150.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for quantifying caries, executed at least in part on data processing hardware, the method comprising:
    generating a digital image of a tooth, the image comprising intensity values for a region of pixels corresponding to the tooth, gum, and background;
    automatically extracting at least one lesion area from sound regions of a tooth by,
        identifying tooth regions and extracting suspicious lesion areas in the identified tooth regions,
        selecting a first subset of the extracted suspicious lesion areas,
        removing false positives in the first subset of the extracted suspicious lesion areas of the tooth by applying an additional false positive detection to the first subset of the extracted suspicious lesion areas to leave a smaller second subset of the first subset, and
        identifying remaining suspicious lesion areas not in the first subset and suspicious lesion areas in the second subset as the extracted at least one lesion area;
    identifying an adjacent sound region that is adjacent to the extracted at least one lesion area;
    reconstructing intensity values for tooth tissue within the extracted at least one lesion area according to values in the adjacent sound region; and
    quantifying the condition of the caries using the reconstructed intensity values and intensity values from the lesion area.

2. The method of claim 1, wherein generating the digital image of the tooth comprises obtaining a fluorescence image of the tooth.

3. The method of claim 1, wherein generating the digital image of the tooth comprises:
    obtaining a fluorescence image of the tooth;
    obtaining a reflectance image of the tooth; and
    combining image data for the fluorescence and reflectance images.

4. The method of claim 1 further comprising identifying one or more tooth regions using thresholding.

5. The method of claim 1, wherein extracting the suspicious lesion area comprises using a marker-controlled watershed algorithm.

6. The method of claim 1, wherein extracting the suspicious lesion area comprises using a morphological bottom-hat based method along with multi-resolution and surface reconstruction techniques.

7. The method of claim 1, wherein removing false positives comprises locating interproximal regions, selecting the first subset of the extracted suspicious lesion areas by identifying suspicious lesion areas in the interproximal regions, and removing interproximal false positives to determine the second subset.

8. The method of claim 1, wherein the step of reconstructing intensity values is performed by a process consisting of one or more bilinear interpolation, surface fit, and interpolation by solving Laplace's equation.

9. The method of claim 1, wherein quantifying the condition of the caries comprises calculating the fluorescence loss of the lesion area or calculating the area of the lesion area.

10. A computer program embodied on a non-transitory computer readable medium for use in quantifying caries, the program comprising executable instructions that when loaded on a computer, causes the computer to:
generate a digital image of a tooth, the image comprising intensity values for a region of pixels corresponding to the tooth, gum, and background;
automatically extract at least one lesion area from sound regions of a tooth by,
identifying tooth regions in the digital image,
extracting suspicious lesion areas in the identified tooth regions, and
locating interproximal regions in the identified tooth regions,
identifying one or more suspicious lesion areas connected to the interproximal regions,
removing false positives in the one or more suspicious lesion areas connected to the interproximal regions by applying an additional interproximal caries detection process, and identifying remaining suspicious lesion areas connected to the interproximal regions and suspicious lesion areas not connected to the interproximal regions as the extracted at least one lesion area;
identify an adjacent sound region that is adjacent to the extracted at least one lesion area;
reconstruct intensity values for tooth tissue within the at least one extracted lesion area according to values in the adjacent sound region; and
quantify the condition of the caries using the reconstructed intensity values and intensity values from the at least one extracted lesion area.

11. The computer program of claim 10 wherein generating the digital image of the tooth comprises obtaining a fluorescence image of the tooth.

12. The computer program of claim 10, wherein generating the digital image of the tooth comprises:
obtaining a fluorescence image of the tooth;
obtaining a reflectance image of the tooth; and
combining image data for the fluorescence and reflectance images.

13. The computer program of claim 10 further comprising identifying one or more tooth regions using thresholding.

14. The computer program of claim 10, wherein extracting the suspicious lesion area comprises using a marker-controlled watershed algorithm.

15. The computer program of claim 10, wherein extracting the suspicious lesion area comprises using a morphological bottom-hat based method along with multi-resolution and surface reconstruction techniques.

16. The computer program of claim 10, wherein the step of reconstructing intensity values is performed by a process consisting of one or more of bilinear interpolation, surface fit, and interpolation by solving Laplace's equation.

17. The computer program of claim 10, wherein quantifying the condition of the caries comprises calculating the fluorescence loss of the lesion area or calculating the area of the lesion area.

18. The computer program of claim 10, wherein locating interproximal regions comprises locating interproximal regions that have clear demarcation with the steps of:
applying a distance transformation to a binary image of the digital image of the tooth to locate the pixel with the largest distance measured from the boundaries of the identified tooth regions in the binary image;
assigning the identified tooth region that is connected to the located pixel as a first object;
assigning the identified tooth region that is not connected to the located pixel as a second object; and
defining the interproximal regions to be the pixels in the background having the same distance to the first and second objects.

19. The computer program of claim 10, wherein locating interproximal regions comprises locating interproximal regions that have no clear demarcation with the steps of:
defining an origin point in a binary image of the tooth;
casting a fan of ray lines from the origin point in a plurality of angles;
defining a contour line at points at which each ray line first encounters the boundary between tooth and background areas,
determining internal and external markers;
applying a marker-controlled watershed transformation to a gradient image of a grayscale version of the digital image with the internal and external markers to form first and second groups of water basins; and
taking the pixels having the same distance to the first and second groups of water basins as interproximal regions.

20. The computer program of claim 10, wherein locating interproximal regions comprises locating interproximal regions that have no clear demarcation with the steps of:
applying a distance transformation to a binary image of the digital image of the tooth, to form a distance image in which each pixel value represents the closest distance of that pixel to the background of the teeth;
determining internal and external markers using the distance image;
applying a marker-controlled watershed transformation to a gradient image of a grayscale version of the digital image with the internal and external markers to form two groups of water basins; and
taking the pixels having the same distance to the two groups of basins as interproximal regions.

* * * * *